(12) United States Patent
Nemoto

(10) Patent No.: US 8,706,199 B2
(45) Date of Patent: *Apr. 22, 2014

(54) LIQUID INJECTOR WITH APPROPRIATE OPERATING CONDITIONS SET BY SELECTING DISPLAYED IMAGE

(71) Applicant: Shigeru Nemoto, Tokyo (JP)

(72) Inventor: Shigeru Nemoto, Tokyo (JP)

(73) Assignee: Nemoto Kyorindo Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/718,359

(22) Filed: Dec. 18, 2012

(65) Prior Publication Data

US 2013/0184575 A1  Jul. 18, 2013

Related U.S. Application Data

(63) Continuation of application No. 10/691,570, filed on Oct. 24, 2003, now Pat. No. 8,359,087.

(30) Foreign Application Priority Data

Feb. 18, 2003 (JP) ................. 2003-039756

(51) Int. Cl.
  *A61B 5/00* (2006.01)
(52) U.S. Cl.
  USPC .......................................... 600/431; 604/31
(58) Field of Classification Search
  USPC ........................................... 600/431; 604/31
  See application file for complete search history.

(56) References Cited

U.S. PATENT DOCUMENTS

| | | |
|---|---|---|
| 3,916,192 A | 10/1975 | Schmitmann et al. |
| 4,309,613 A | 1/1982 | Brunn et al. |
| 4,466,033 A | 8/1984 | Jordan et al. |
| 4,641,242 A | 2/1987 | Kimura |
| 4,773,086 A | 9/1988 | Fujita et al. |
| 4,978,335 A | 12/1990 | Arthur, III |
| 5,104,374 A | 4/1992 | Bishko et al. |
| 5,469,849 A | 11/1995 | Sasaki et al. |
| 5,533,514 A | 7/1996 | Lavigne et al. |
| 5,681,286 A | 10/1997 | Niehoff |
| 5,778,882 A | 7/1998 | Raymond et al. |
| 5,806,519 A | 9/1998 | Evans et al. |

(Continued)

FOREIGN PATENT DOCUMENTS

| | | |
|---|---|---|
| JP | 02-261431 | 10/1990 |
| JP | 2000-506398 | 5/2000 |

(Continued)

OTHER PUBLICATIONS

Office Action issued Jul. 21, 2010, in Japanese Patent Application No. 2003-39756, filed Feb. 18, 2003.

*Primary Examiner* — Jonathan Cwern

(74) *Attorney, Agent, or Firm* — Oblon, Spivak, McClelland, Maier & Neustadt, L.L.P.

(57) ABSTRACT

A contrast liquid injector has a controller that calculates a necessary volume of the contrast medium based on a read out necessary dose of effective component per unit weight, weight of the subject, and concentration of the effective component. The injection rate of a base-operation condition is changed based on the calculated necessary volume of the contrast medium, wherein the predetermined injection time is unchanged, for all volumes of the contrast medium, when making the injection pattern, whereby a timing of an optimum concentration of the contrast medium will be substantially unchanged for all volumes of the contrast medium.

16 Claims, 13 Drawing Sheets

(56) References Cited

U.S. PATENT DOCUMENTS

| | | |
|---|---|---|
| 5,823,993 A | 10/1998 | Lemelson |
| 5,840,026 A | 11/1998 | Uber et al. |
| 5,865,744 A | 2/1999 | Lemelson |
| 5,919,135 A | 7/1999 | Lemelson |
| 6,132,218 A | 10/2000 | Benja-Athon |
| 6,366,683 B1 | 4/2002 | Langlotz |
| 6,504,897 B1 | 1/2003 | Yonekawa |
| 2002/0007116 A1 | 1/2002 | Zatezalo et al. |
| 2003/0018252 A1 | 1/2003 | Duchon et al. |
| 2004/0078215 A1 | 4/2004 | Dahlin et al. |
| 2004/0081341 A1 | 4/2004 | Cherek et al. |
| 2004/0136578 A1 | 7/2004 | Sieracki et al. |

FOREIGN PATENT DOCUMENTS

| | | |
|---|---|---|
| JP | 2000-189515 | 7/2000 |
| JP | 2001-000429 | 1/2001 |
| JP | 2002-011096 | 1/2002 |
| JP | 2002-102343 | 4/2002 |
| WO | WO 97/12550 | 4/1997 |
| WO | WO 00/64353 | 11/2000 |

US 8,706,199 B2

LIQUID INJECTOR WITH APPROPRIATE OPERATING CONDITIONS SET BY SELECTING DISPLAYED IMAGE

The present application is a continuation application of U.S. patent application Ser. No. 10/691,570, filed on Oct. 24, 2003, the entire contents of U.S. patent application Ser. No. 10/691,570 are incorporated herein by reference, and claims priority to Japanese application 2003-039756, filed Feb. 18, 2003.

BACKGROUND OF THE INVENTION

1. Field of the Invention

The present invention relates to a liquid injector for injecting a liquid into a subject, and more particularly to a liquid injector for injecting a liquid into a subject who is to be imaged by an imaging diagnostic apparatus such as a CT (Computed Tomography) apparatus, an MRI (Magnetic Resonance Imaging) apparatus, an angiography apparatus, or the like.

2. Description of the Related Art

Presently available imaging diagnostic apparatus for capturing fluoroscopic images of subjects include CT scanners, MRI apparatus, PET (Positron Emission Tomography) apparatus, ultrasonic diagnostic apparatus, angiography apparatus, MRA (MR Angiography) apparatus, and ultrasonograph.

When such an imaging diagnostic apparatus is used to capture a fluoroscopic image of a subject, it is occasionally practiced to inject a liquid such as a contrast medium or a saline solution into the subject. There has been put to practical use a liquid injector for automatically injecting a liquid into a subject. Such a liquid injector has a drive motor and a slider mechanism, and employs a liquid syringe that is removably mounted.

The liquid syringe comprises a cylinder and a piston slidably inserted in the cylinder. The cylinder is filled with a liquid such as a contrast medium or a saline solution to be injected into the subject. The liquid syringe is connected to the subject by an extension tube and set on a liquid injection mechanism. The liquid injection mechanism individually holds the piston and the cylinder and moves them relatively to each other for injecting a liquid, typically a contrast medium, from the liquid syringe into the subject.

The operator determines the rate at which the contrast medium is to be injected and the total amount of the contrast medium to be injected, in view of various conditions, and then enters data representing the rate and total amount into the liquid injection mechanism. Based on the entered data, the liquid injection mechanism injects the contrast medium into the subject. The injected contrast medium changes the image contrast of the subject, allowing the imaging diagnostic apparatus to capture a good fluoroscopic image of the subject.

Some liquid injectors are capable of injecting a saline solution as well as a contrast medium into the subject. For operating such a liquid injector, the operator enters, if desired, an instruction to inject the saline solution following the completion of the injection of the contrast medium, together with data representing the rate at which the saline solution is to be injected and the total amount of the saline solution to be injected, into the liquid injector.

Based on the entered data, the liquid injector first injects the contrast medium and then automatically injects the saline solution after the contrast medium has been injected. The subsequently injected saline solution pushes the previously injected contrast medium, reducing the consumption of the contrast medium, and also reduces artifacts in the captured image.

Liquid injectors of the type described above have been devised and applied for patent by the applicant of the present application (see, for example, patent documents 1, 2 below).

Patent document 1: Japanese laid-open patent publication No. 2002-11096;

Patent document 2: Japanese laid-open patent publication No. 2002-102343.

The above liquid injector is capable of injecting a contrast medium into the subject in order to change the image contrast of the subject to a state which allows the imaging diagnostic apparatus to capture a good fluoroscopic image of the subject.

For injecting an appropriate amount of contrast medium at an appropriate rate into the subject, the operator is required to determine the rate at which the contrast medium is to be injected and the total amount of the contrast medium to be injected, in view of various conditions including an area to be imaged of the subject and the weight of the subject, and enter numerical data representing the rate and the total amount into the liquid injector. This process is too complex for unskilled operators to carry out easily, and does not prevent inappropriate numerical values to be entered into the liquid injector.

In particular, since a plurality of different types of contrast mediums containing effective components which have different concentrations are now available on the market, the operator needs to determine and enter the rate at which the contrast medium is to be injected and the total amount of the contrast medium to be injected, also in view of the type of the contrast medium to be used. This situation makes the entire data entry process more complex, and poses an increased burden on the operator in determining and entering the above data for both a contrast medium and a saline solution if the operator is operating a liquid injector which is capable of injecting both the contrast medium and the saline solution.

SUMMARY OF THE INVENTION

It is therefore an object of the present invention to provide a liquid injector which allows the operator to inject a contrast medium into a subject through a simple operating process.

According to the present invention, in order to inject at least a contrast medium into a subject whose fluoroscopic image is to be captured by an imaging diagnostic apparatus, a liquid injector has a liquid injection mechanism, a condition storage means, an image storage means, a section display means, a section input means, a region displaying means, region input means, an operation reading means, and an injection control means.

The condition storage means stores data of operating conditions of the liquid injection mechanism for each of a plurality of regions to be imaged of a human body. The image storage means stores data of schematic images of a plurality of body sections of the human body and schematic images of a plurality of regions to be imaged of the human body in association with each other. The section display means displays the schematic images of the body sections in the shape of a human body. The section input means accepts an input action to select one of the displayed schematic images of the body sections. The region displaying means displays the schematic image of at least one of the regions to be imaged in relation to the selected schematic image of the body section. The region input means accepts an input action to select the displayed schematic image of at least one of the regions to be imaged. The operation reading means reads the data of operating conditions corresponding to the selected schematic image of at least one of the regions to be imaged. The injection control means controls operation of the liquid injection mechanism under the operating conditions whose data have been read.

When the operator manually selects one of the schematic images of body sections and then one of the schematic images of regions to be imaged, the liquid injector injects a contrast medium into the subject under optimum operating conditions for the selected region to be imaged. Thus, the contrast medium can be injected into the subject under optimum conditions through a simple process. As the operator is not required to perform a complex procedure for entering numerical values of an injection rate and a total amount of contrast medium to be injected, the contrast medium is prevented from being injected into the subject under inappropriate conditions due to a mistake that the operator might otherwise make in entering those numerical values.

The various means referred to in the present invention may be arranged to perform their stated functions, and may be implemented by dedicated pieces of hardware for performing the functions, data processing apparatus for performing the functions according to computer programs, functions achieved in data processing apparatus according to computer programs, or combinations thereof The various means referred to in the present invention are not required to be individually independent entities, and may be arranged such that a plurality of means may be constructed as a single apparatus, a certain means may be part of another means, or part of a certain means and part of another means overlap each other.

A computer unit referred to in the present invention may comprise a piece of hardware capable of reading the data of a computer program and performing a processing operation according to the computer program, and may comprise a CPU (Central Processing Unit) to which are connected various devices including a ROM (Read Only Memory), a RAM (Random Access Memory), an IX (Interface) unit, etc.

According to the present invention, enabling a computer unit to carry out various operations according to a computer program also signifies enabling the computer unit to control operation of various devices to carry out various operations. For example, storing various data in a computer unit may signify enabling a CPU to store various data in an information storage medium such as a RAM or the like fixedly mounted in the computer unit, or enabling a CPU to store various data in an information storage medium such as an FD (Flexible Disc-cartridge) or the like replaceably loaded in the computer unit through an FDD (FD Drive).

An information storage medium referred to in the present invention may comprise a piece of hardware which stores in advance a computer program for enabling a computer unit to perform various processing operations. An information storage medium may comprise, for example, a ROM or an HDD (Hard Disc Drive) fixedly mounted in the computer unit, or a CD (Compact Disc)-ROM or an FD replaceably loaded in the computer unit.

The above and other objects, features, and advantages of the present invention will become apparent from the following description with reference to the accompanying drawings which illustrate examples of the present invention.

DETAILED DESCRIPTION OF THE PREFERRED EMBODIMENTS

Figure 4:
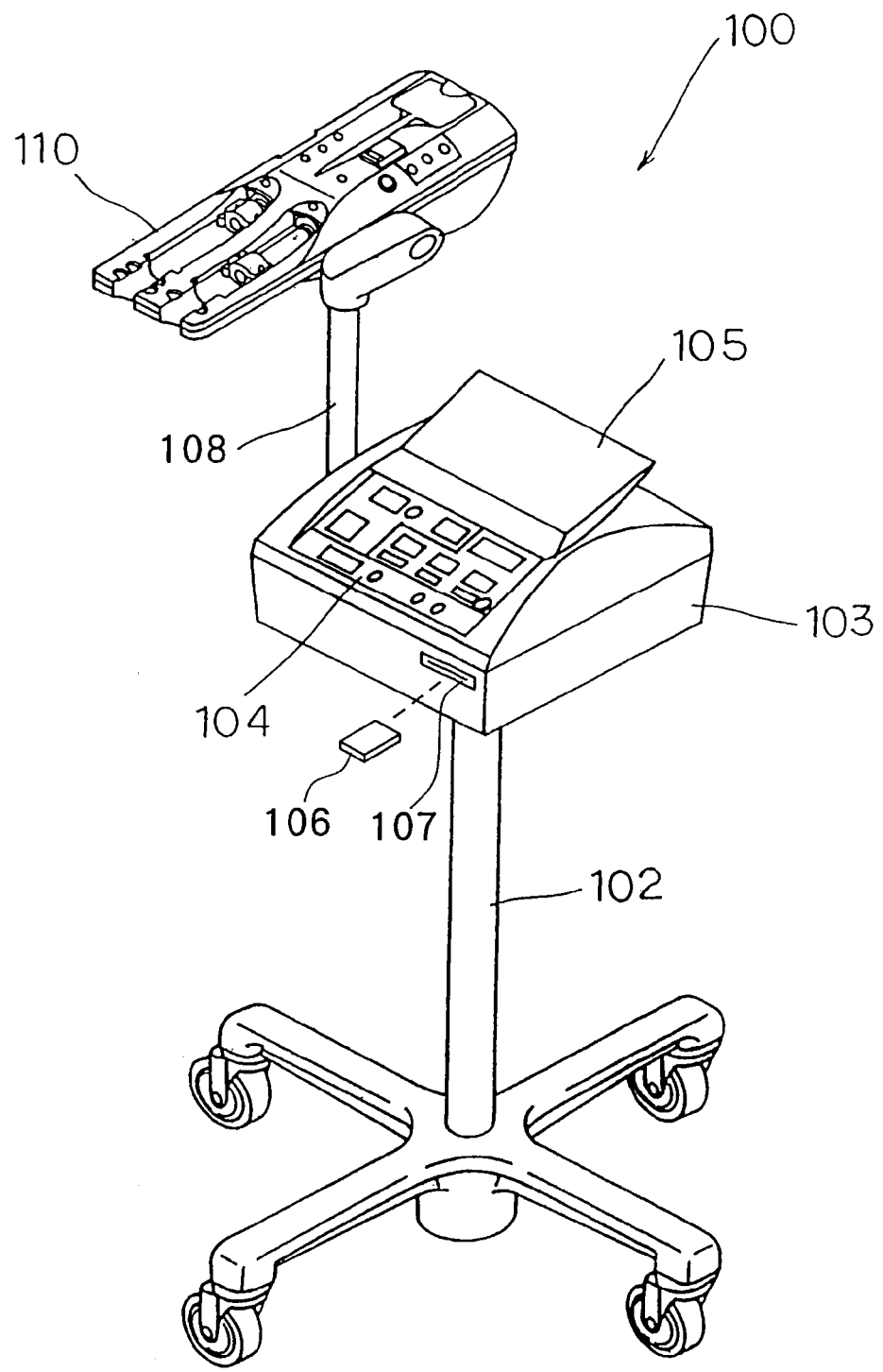
FIG. 4 is a perspective view of the liquid injector.

A liquid injector according to an embodiment of the present invention will be described below with reference to the drawings. As shown in FIG. 4, a liquid injector 100 according to an embodiment of the present invention has main body 103 mounted on the upper end of stand 102. Main body 103 supports thereon console panel 104, touch panel 105 as a display panel, and card drive 107 for PC card 106 which serves as an information storage medium.

Movable arm 108 is vertically mounted on a side wall of main body 103, and injection head 110 as a cylinder holder is mounted on the upper end of movable arm 108.

Figure 3:
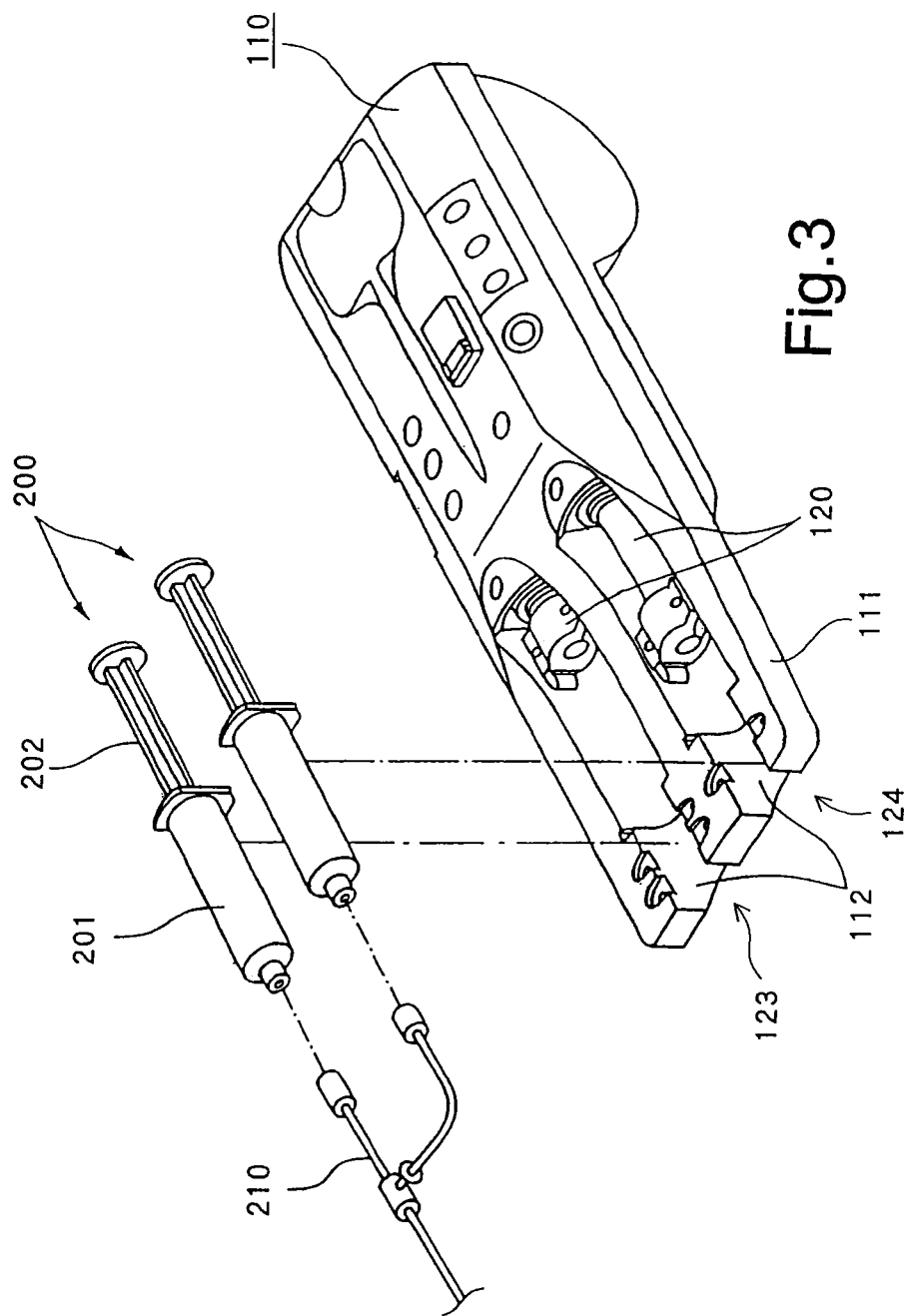
FIG. 3 is a perspective view of the liquid injector, showing the manner in which liquid syringes are set on an injection head of the liquid injector.

As shown in FIG. 3, injection head 110 has two recesses 112 defined as a syringe holding mechanism in an upper surface of cylinder holder 111. Cylinders 201 of liquid syringes 220 are removably held in respective recesses 112. Each liquid syringe 220 comprises cylinder 201 and piston 202 slidably inserted in cylinder 201.

Two piston actuating mechanisms 120 are disposed respectively behind recesses 112 in injection head 110 for individually gripping and sliding pistons 202 of syringes 200 that are held in respective recesses 112.

Each of piston actuating mechanisms 120 has drive motor 121 (see FIG. 2) such as an ultrasonic motor or the like as a drive source for sliding piston 202 back and forth through a screw mechanism (not shown) or the like.

Piston actuating mechanisms 120 also have respective load cells 122 as pressure-sensitive devices for individually detecting pressures under which pistons 202 of syringes 200 are pressed.

Liquid syringe 200 which is filled with a contrast medium as a liquid and another liquid syringe 200 which is filled with a saline solution as another liquid are set respectively in two recesses 112 in injection head 110. Two recesses 112 and two piston actuating mechanisms 120 make up liquid injection mechanisms including medium injection mechanism 123 for injecting a contrast medium into a subject and solution injection mechanism 124 for injecting a saline solution into a subject.

Figure 5:
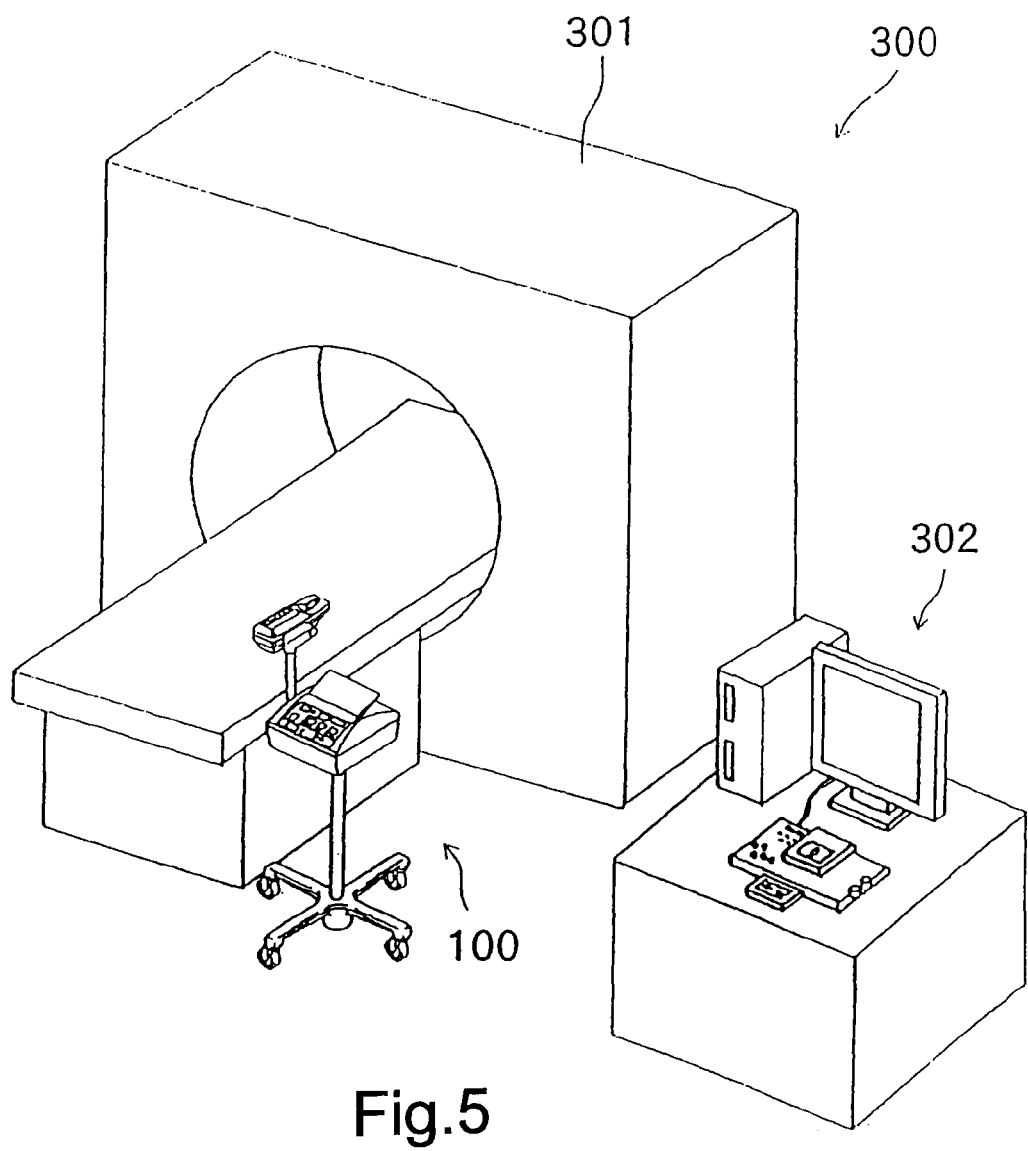
FIG. 5 is a perspective view of a CT scanner as an imaging diagnostic apparatus.

As shown in FIG. 5, liquid injector 100 is positioned near CT scanner 300 which serves as an imaging diagnostic apparatus. Liquid injector 100 injects a contrast medium and a saline solution into a subject who is to be imaged by CT scanner 300.

CT scanner 300 has imaging unit 301 and control unit 302 which is connected on-line to liquid injector 100.

Figure 2:
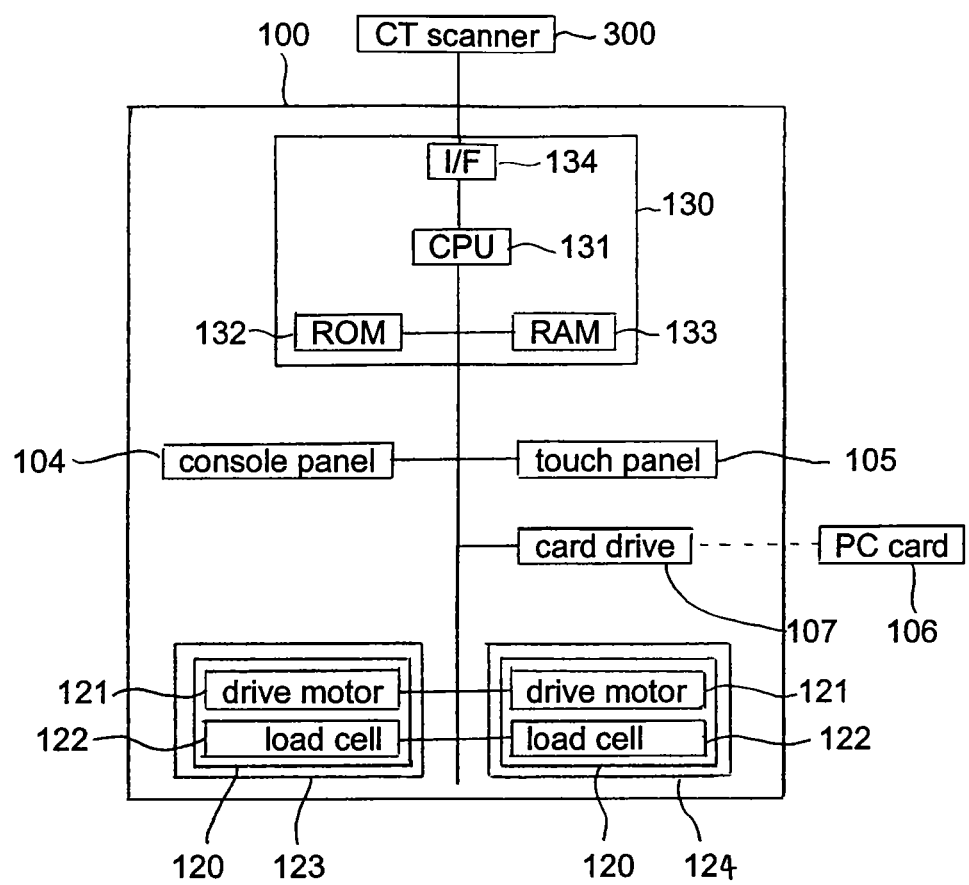
FIG. 2 is a block diagram of a circuit arrangement of the liquid injector.

As shown in FIG. 2, liquid injector 100 has computer unit 130 connected to drive motors 121 of two syringe actuating mechanisms 120, console panel 104, and touch panel 105.

Computer unit 130 comprises a so-called one-chip microcomputer, and has pieces of hardware including CPU (Central Processing Unit) 131, ROM (Read Only Memory) 132, RAM (Random Access Memory) 133, and I/F (Interface) 134.

Computer unit 130 has a suitable computer program installed in the form of firmware in an information storage medium such as ROM 132. CPU 131 performs various processing operations according to the installed computer program.

Figure 1:
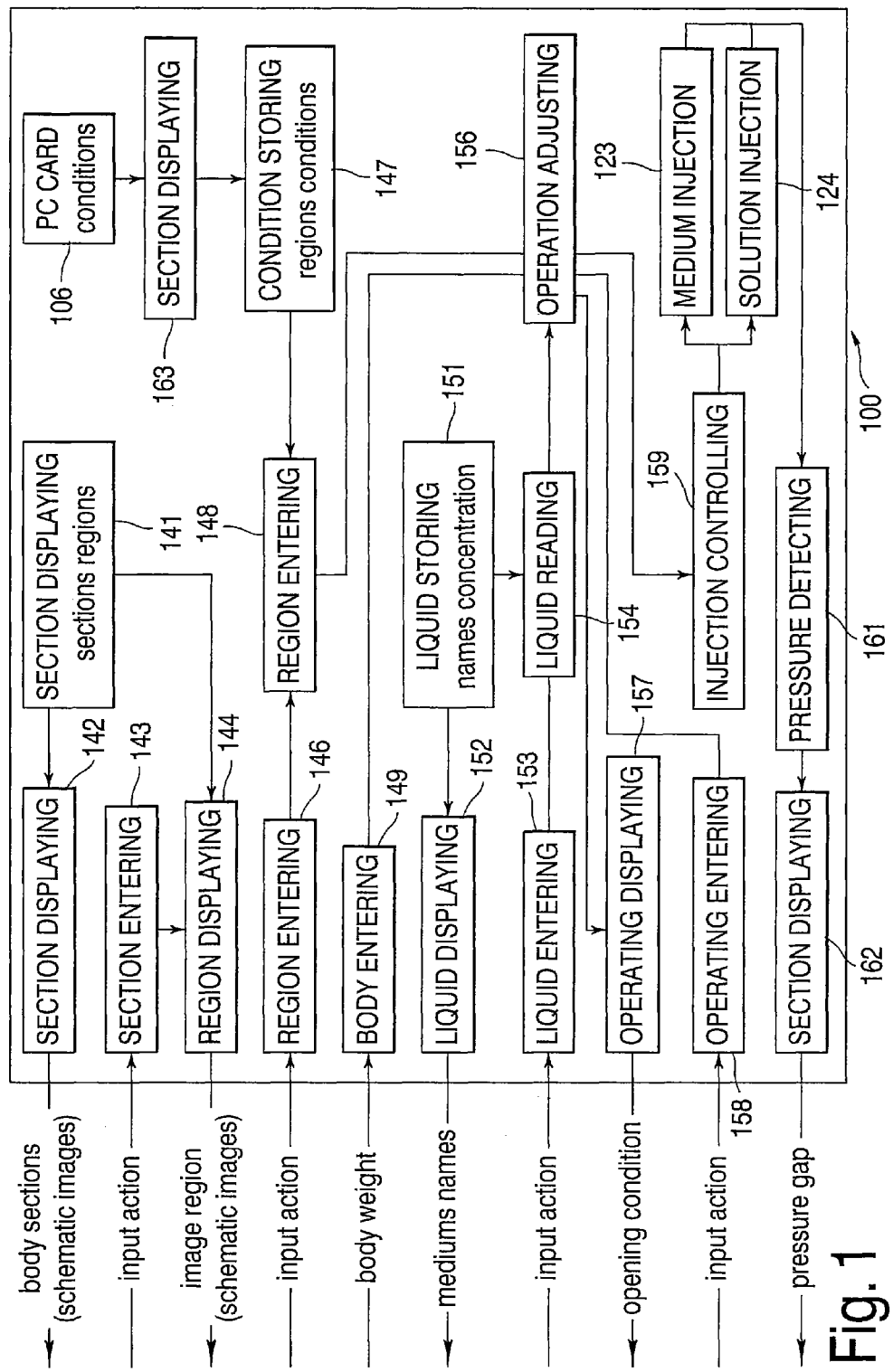
FIG. 1 is a block diagram showing a logic structure of a liquid injector according to an embodiment of the present invention.

By operating according to the installed computer program, computer unit 130 logically has various functions as various means which include, as shown in FIG. 1, image storing function 141, section displaying function 142, section entering function 143, region displaying function 144, region entering function 146, condition storing function 147, operation reading function 148, body entering function 149, liquid storing function 151, liquid displaying function 152, liquid entering function 153, liquid reading function 154, operation adjusting function 156, operation displaying function 157, operation entering function 158, injection controlling function 159, pressure detecting function 160, pressure displaying function 162, condition updating function 163, etc.

Storing functions 141, 151, 147 correspond to storage areas set up in RAM 133 for CPU 131 to recognize data stored therein according to the computer program. Reading functions 148, 154 correspond to functions of CPU 131 to read stored data from RAM 133.

Displaying functions 142, 144, 152, 157, 162 correspond to functions of CPU 131 to display stored data from RAM 133 on touch panel 105. Entering functions 143, 146, 149, 153, 158 correspond to functions of CPU 131 to recognize data based on input actions on touch panel 105.

Image storing function 141 stores data of schematic images of a plurality of body sections of a human body and data of schematic images of a number of regions to be imaged in relation to each other. Section displaying function 142 displays schematic images of body sections whose data are stored by image storing function 141 in the shape of a human body.

Section entering function 143 accepts an input action to select one of the body sections displayed by section displaying function 142. Region displaying function 144 displays a schematic image of at least one region to be imaged which corresponds to the body section selected by section entering function 143. Region entering function 146 accepts an input action to select the region to be imaged whose image has been displayed by region displaying function 144.

Figure 6:
FIG. 6 is a schematic front elevational view showing an initial displayed image on a touch panel as a display panel.

More specifically, liquid injector 100 defines "head part, chest part, abdomen part, and leg part" as a plurality of body sections, and data of schematic images corresponding to those body sections are registered in ROM 132. When a certain action is performed on liquid injector 100, schematic images of "head part, chest part, abdomen part, and leg part" in association with body shapes are displayed on an upper screen area of touch panel 105 as shown in FIG. 6.

Data of schematic images of "brain part, jaw part, and neck part" are registered as a plurality of regions to be imaged in relation to the schematic image of the body section "head part". Similarly, data of schematic images of "heart part" and "lung part" are registered in relation to the schematic image of the body section "chest part", data of schematic images of "stomach part, liver part, . . . " are registered in relation to the schematic image of the body section "abdomen part", and data of images of "upper part and lower part" are registered in relation to the schematic image of the body section "leg part".

Figure 7:
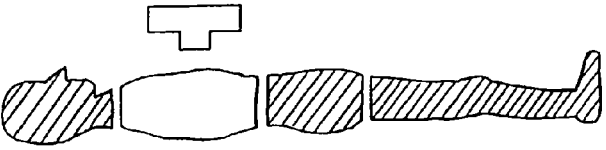
FIG. 7 is a schematic front elevational view showing a displayed image at the time a body section is selected.

When one of the schematic images of the body sections displayed as a human body shape on touch panel 105 is manually acted upon, a schematic image of a scanner mechanism is displayed above only the schematic image that is acted upon, and that schematic image is highlighted with the other schematic images darkened, as shown in FIG. 7.

Figure 8:
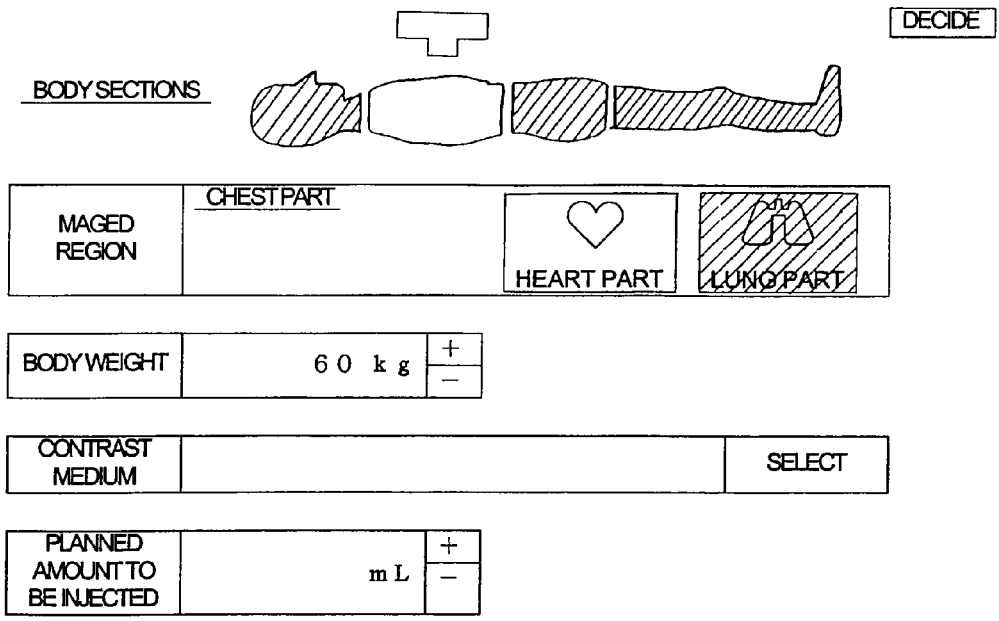
FIG. 8 is a schematic front elevational view showing a displayed image at the time a to-be-imaged region is selected.

At the same time, the schematic images of the regions that are related to the highlighted image are displayed below the displayed schematic images of the body sections. When one of the displayed schematic images of the related regions is manually acted upon, that schematic image is highlighted with the other schematic images darkened, as shown in FIG. 8.

Condition storing function 147 stores data representative of operating conditions of medium injection mechanism 123 and solution injection mechanism 124 for each of the human body regions to be imaged. More specifically, since liquid injector 100 according to the present embodiment injects a contrast medium and then a saline solution into the subject, the data representative of the operating conditions are established in order to interlink injecting operations of medium injection mechanism 123 and solution injection mechanism 124.

Figure 10:
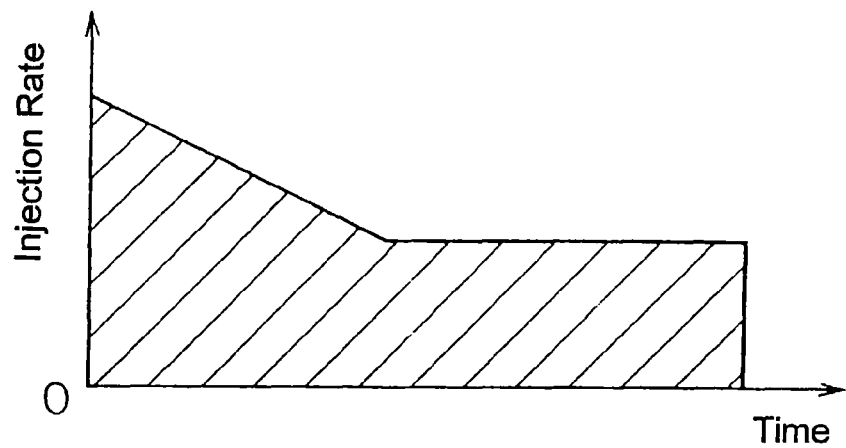
FIG. 10 is a diagram showing a variable pattern of an injection rate as an operating condition.

The data representative of the operating conditions of medium injection mechanism 123 are established to change the rate at which the contrast medium is injected, with time according to a variable pattern such that the contrast of a fluoroscopic image achieved by the contrast medium will approximate an optimum level. The variable pattern is set to an optimum pattern based on experimental results. For example, as shown in FIG. 10, the variable pattern is set such that the injection rate is linearly reduced for a certain period of time from the start of injection, and subsequently kept constant.

Figure 9:
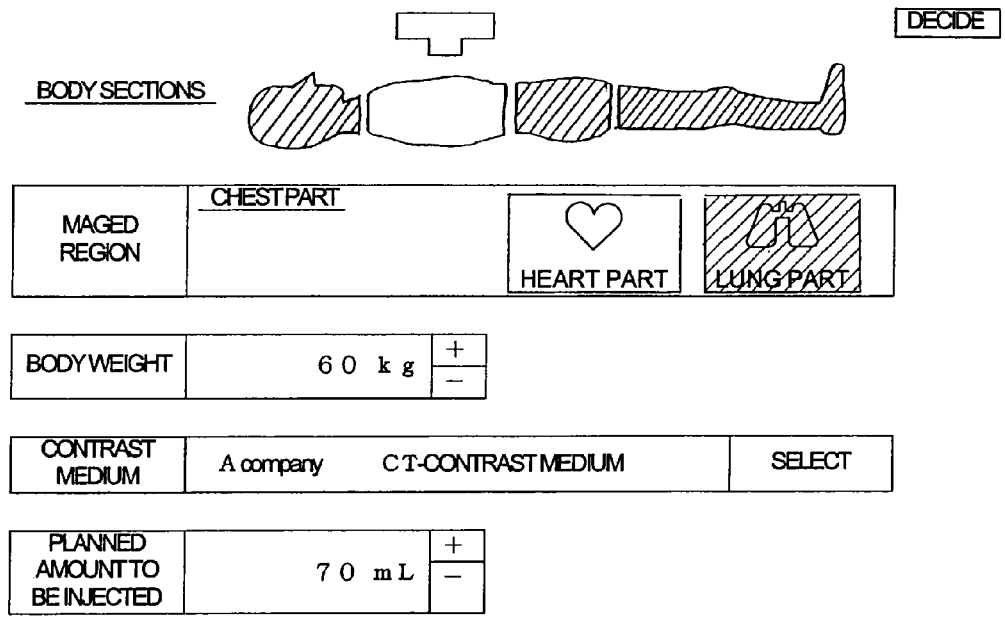
FIG. 9 is a schematic front elevational view showing a displayed image at the time various data are entered.

Operation reading function 148 reads data of operating conditions for the region to be imaged which has been selected by region entering function 146 from condition storing function 147. Body entering function 149 accepts an input action to enter a body weight as a human body item related to the capturing of a fluoroscopic image, as shown in FIG. 9.

Liquid storing function 151 stores data of the concentration of iodine which is an effective component as a liquid item related to the capturing of a fluoroscopic image, with respect to each of the product names of a plurality of types of contrast mediums. Specifically, liquid injector 100 can use a plurality of types of contrast mediums, which contain different concentrations of iodine for the respective products. When a contrast medium is injected into a subject and the subject is imaged to capture a fluoroscopic image thereof, since a different iodine concentration results in a different contrast, liquid injector 100 has data of iodine concentrations registered for the respective names of products as contrast mediums.

Liquid displaying function 152 displays the product names of contrast mediums whose data are registered. Liquid entering function 153 accepts an input action to select one of the types of contrast mediums which have been displayed by liquid displaying function 152. Liquid reading function 154 reads data of the iodine concentration which corresponds to the contrast medium selected by liquid entering function 153.

Operation adjusting function 156 corresponds to a function of CPU 131 to carry out a predetermined processing operation. Specifically, operation adjusting function 156 adjusts operating conditions whose data have been read by operation reading function 148, depending on the body weight entered by body entering function 149 and the iodine concentration read by liquid reading function 154.

More specifically, liquid injector 100 has registered data of a variable pattern according to which the injection rate varies with time, as an operating condition for injecting the contrast medium. The variable pattern is set so as to satisfy a predetermined total amount of contrast medium to be injected.

The data of the total amount of iodine as a contrast medium which corresponds to the body weight of the subject is registered as "A(g/Kg)" based on experimental results. If the body weight of the subject is entered as "B(Kg)", for example, then the total amount of iodine to be injected which is proportional to the body weight is calculated as "A.times.B(g)". If the data of the iodine concentration of the contrast medium is read as "C (g/ml)", for example, then the total amount of the contrast medium to be injected which is inversely proportional to, the iodine concentration is calculated as "(A.times.B)C (ml)". When the total amount of the contrast medium to be injected is thus calculated, if the data of the injection rate is registered according to a variable pattern having a waveform as shown in FIG. 10, then the waveform of the variable pattern is vertically moved while the period of time consumed to inject the contrast medium remains unchanged, so that the area surrounded by the waveform, the x-axis, and the y-axis corresponds to the total amount of the contrast medium to be injected.

Operation displaying function 157 displays the total amount of the contrast medium to be injected which is an operating condition adjusted by operation adjusting function 156. Operation entering function 158 accepts a manual input action for correcting the data of the total amount of the contrast medium to be injected which is displayed by operation displaying function 157. When the data of the total amount of the contrast medium to be injected is corrected by operation entering function 158 and entered, operation adjusting function 156 adjusts the total amount of the contrast medium to be injected depending on the entered data.

Injection controlling function 159 corresponds to a function for CPU 131 to energize drive motors 121 of medium injection mechanism 123 and solution injection mechanism 124 depending on the processed data, and controls the operation of medium injection mechanism 123 and solution injection mechanism 124 under the operating conditions adjusted by operation adjusting function 156.

Pressure detecting function 161 corresponds to a function for CPU 131 to recognize data of pressures detected by load cells 122 of medium injection mechanism 123 and solution injection mechanism 124. Pressure detecting function 161 detects in real-time the pressures of the contrast medium and the saline solution which are injected into the subject. Pressure displaying function 162 generates in real-time data of a time-dependent pressure graph from the pressures of the contrast medium and the saline solution which are detected by pressure detecting function 161, and displays in real-time the time-dependent pressure graph.

Condition updating function 163 corresponds to a function for CPU 131 to control operation of card drive 107. When PC card 106 which stores the registered data of operating conditions is loaded into card drive 107, card drive 107 reads the registered data of operating conditions from PC card 106, and updates the data of operating conditions in condition storing function 147.

While part of the above various functions of liquid injector 100 is accomplished by pieces of hardware such as console panel 104, they are mainly implemented by CPU 131 as a piece of hardware as it functions according to resources stored in an information storage medium such as ROM 132, etc., and the computer program.

Such resources include a data file of schematic images of a plurality of body sections of a human being and schematic images of a number of regions to be imaged in relation to each other, a data file of operating conditions of medium injection mechanism 123 and solution injection mechanism 124 for each of the human body regions to be imaged, a data file of iodine concentrations for the respective names of products as contrast mediums, etc.

The above computer program is stored in an information storage medium such as RAM 133 or the like as software to be executed by CPU 131 for displaying schematic images of a plurality of body sections whose data have been registered in RAM 133, for example, in the shape of a human body on touch panel 105, receiving an input action made on touch panel 105 to select one of the displayed body sections, displaying a schematic image of at least one region to be imaged which corresponds to the selected body section, receiving an input action to select the region to be imaged whose image has been displayed, reading data of operating conditions corresponding to the selected body region, receiving an input action to enter the body weight, displaying the product names of a plurality of contrast mediums whose data have been registered, receiving an input action to select one of the displayed types of contrast mediums, reading data of an iodine concentration corresponding to the selected type of contrast medium, adjusting the operating conditions whose data have been read depending on the entered body weight and the iodine concentration whose data have been read, displaying a total amount of contrast medium to be injected which is represented by the adjusted operating conditions, receiving a manual action to correct the data of the displayed total amount of contrast medium to be injected, adjusting the total amount of contrast medium to be injected depending on the input data, controlling operation of medium injection mechanism 123 and solution injection mechanism 124 under the adjusted operating conditions, detecting in real-time with load cell 122 pressures of the contrast medium and saline solution which are injected into the subject by medium injection mechanism 123 and solution injection mechanism 124, generating and displaying data of a time-dependent graph of the detected pressures of the contrast medium and saline solution, reading data of operating conditions from PC card 106 loaded in card drive 107 and updating data of operating conditions in RAM 133.

Operation of the Liquid Injector:

For using liquid injector 100 of the above construction, the operator (not shown) positions liquid injector 100 near imaging unit 301 of CT scanner 300 as shown in FIG. 5. Then, as shown in FIG. 3, the operator connects two liquid syringes 200 to the subject (not shown) placed in imaging unit 301 with bifurcated extension tube 210. Cylinders 201 of liquid syringes 200 are held in respective recesses 122 of injection head 110, and pistons 202 are gripped by syringe actuating mechanisms 120.

Then, the operator makes an input action on console panel 104 to instruct liquid injector 100 to start operating. Touch panel 105 then displays an initial image on its display screen in step S1 shown in FIG. 12. As shown in FIG. 6, the initial image contains various input items arranged successively downwardly according to an input sequence. The initial image includes in its uppermost portion schematic images of a plurality of body sections in the shape of a human body.

If the operator touches, with a fingertip, one of the schematic images of the body sections displayed on touch panel 105 to select the touched schematic image of the body section in step S2, then, as shown in FIG. 7, the selected schematic image of the body section is highlighted with the other schematic images darkened, and a schematic image of a scanner mechanism is also displayed above the selected schematic image of the body section.

At the same time, schematic images of a plurality of regions to be imaged which are related to the selected body section are read and displayed below the displayed schematic images of the body sections in steps S3, S4. If the operator touches one of the schematic images of the regions to select the touched schematic image of the region in step S5, then only the selected schematic image of the region is highlighted with the other schematic images darkened, as shown in FIG. 8.

When the region to be imaged is thus selected, liquid injector 100 reads data of operating conditions corresponding to the selected region to be imaged from RAM 133 in step S6, and also reads a default body weight and the product name of the previously used contrast medium in step S7.

As shown in FIG. 9, the default body weight and the product name of the previously used contrast medium are set as data and displayed in step S8, and the operating conditions are adjusted according to the body weight and the product name in step S9. When the operating conditions are thus adjusted, a total amount of contrast medium to be injected is calculated and also displayed in step S10.

Figure 13:
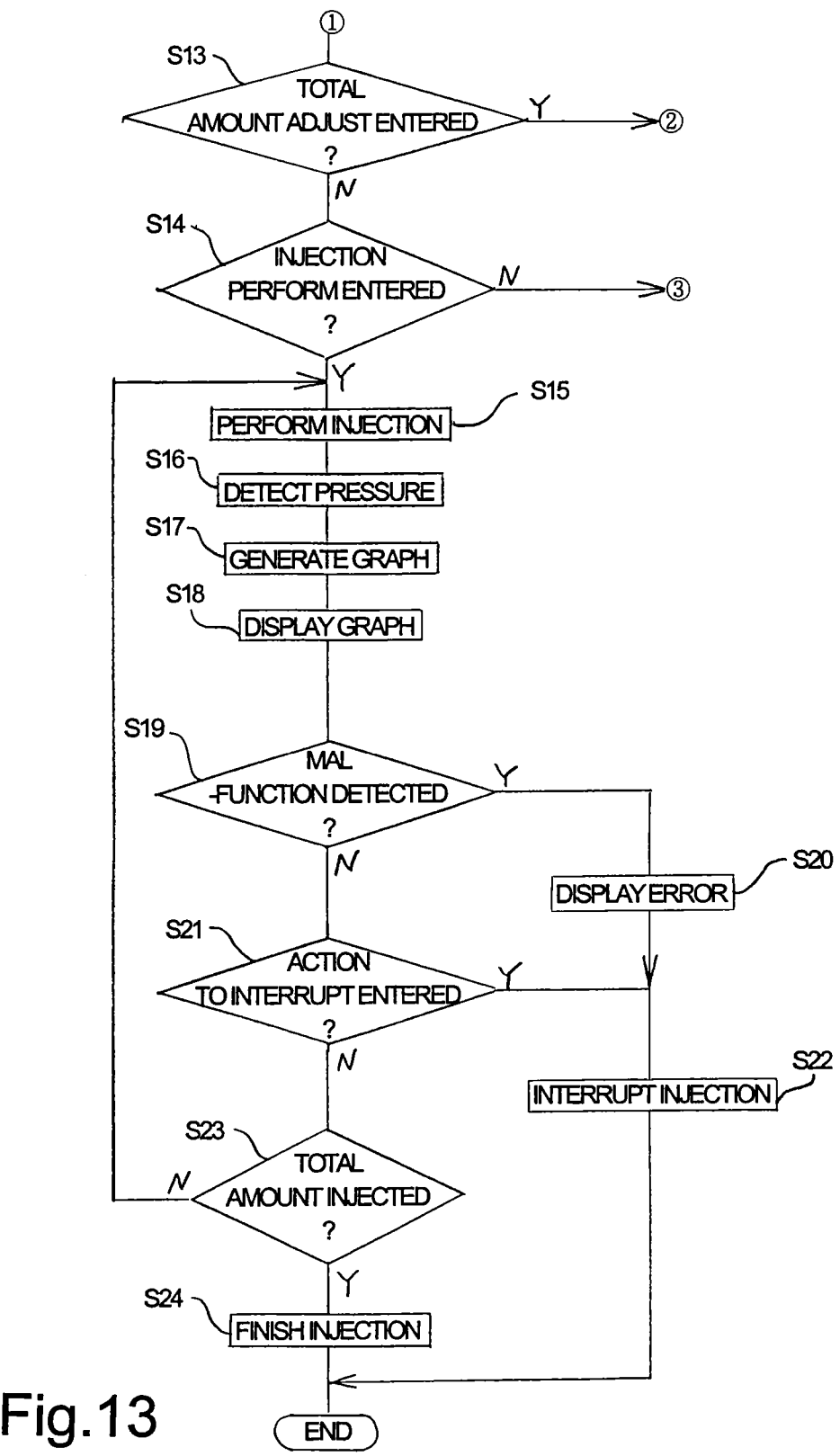
FIG. 13 is a flowchart of a latter part of the processing sequence of the liquid injector.

The operator confirms the body weight, the product name, and the total amount of contrast medium to be injected which are displayed. If the operator finds them satisfactory, then the operator touches, with a fingertip, an icon "DECIDE" displayed at an upper right corner of the display screen in step S14 shown in FIG. 13. Liquid injector 100 then controls operation of medium injection mechanism 123 and solution injection mechanism 124 under the adjusted operating conditions to inject the contrast medium and saline solution into the subject in step S15.

Figure 12:
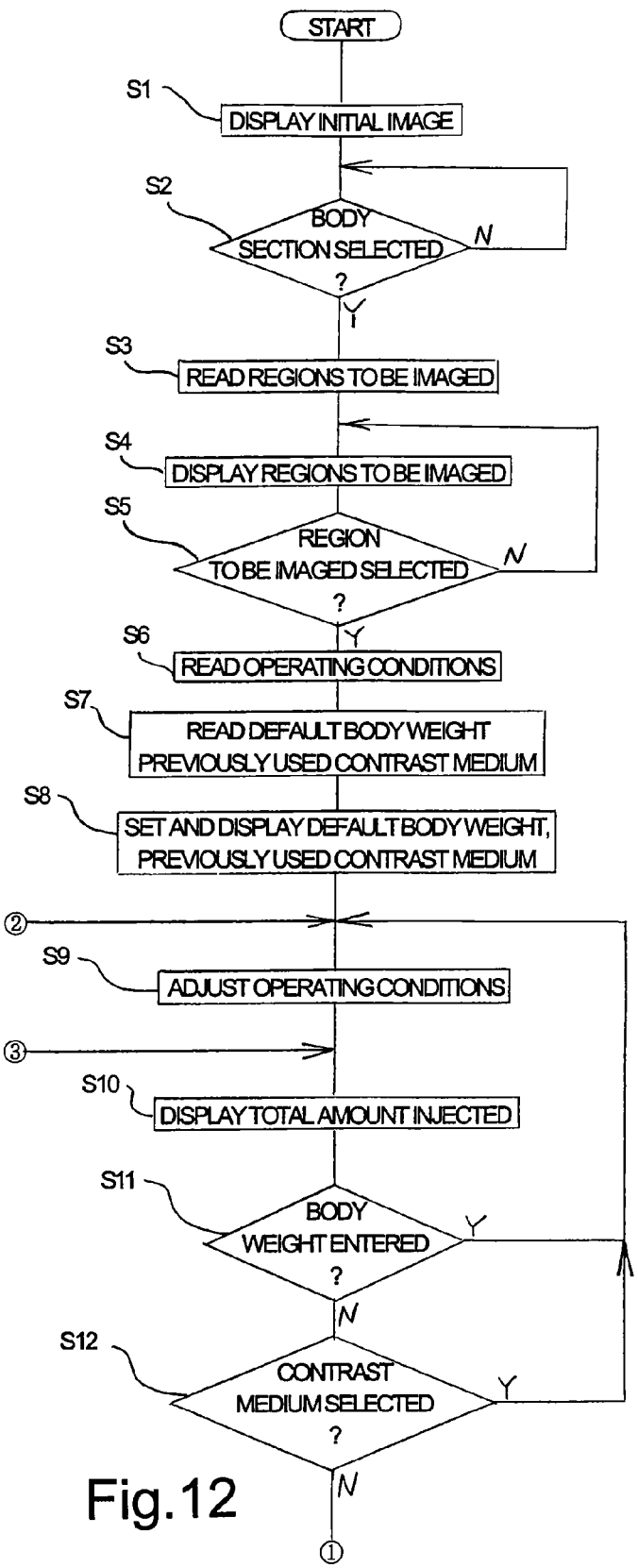
FIG. 12 is a flowchart of a former part of a processing sequence of the liquid injector.

After the operator has confirmed the body weight, the product name, and the total amount of contrast medium to be injected, if the operator wants to enter a body weight, then the operator touches, with a fingertip, an icon "+/−" displayed to the right of the item "BODY WEIGHT" in step S11 shown in FIG. 12. The displayed numerical value of the body weight then changes, and the operating conditions are adjusted depending on the changed body weight in step S9.

If the operator wants to enter a type of contrast medium, then the operator touches, with a fingertip, an icon "SELECT" displayed to the right of the item "CONTRAST MEDIUM" in step S12. Then, product names of contrast mediums whose data have been registered are displayed on a pull-up menu or the like. The operator selects and touches, with a fingertip, one of the displayed product names of the contrast mediums. The selected product name of the contrast medium is now set and displayed. The data of an iodine concentration of the selected contrast medium is read, so that the operating conditions are adjusted depending on the iodine concentration in step S9.

If the operator wants to directly enter a total amount of contrast medium to be injected, then the operator touches, with a fingertip, an icon "+/−" displayed to the right of the item "PLANNED AMOUNT TO BE INJECTED" in step S13. The displayed numerical value of the total amount of contrast medium to be injected is changed, and the operating conditions are adjusted depending on the changed total amount of contrast medium to be injected in step S9.

After having confirmed the body weight, the product name, and the total amount of contrast medium to be injected, as described above, the operator touches, with a fingertip, the icon "DECIDE" displayed at the upper right corner of the display screen in step S14. Liquid injector 100 now controls operation of drive motor 121 of medium injection mechanism 123 under the adjusted operating conditions in step S15.

As shown in FIG. 10, the total amount of contrast medium is injected into the subject according to the variable pattern which is set such that the injection rate is linearly reduced for a certain period of time from the start of injection, and subsequently kept constant. After the injection of the contrast medium is completed, an amount of saline solution proportional to the contrast medium is injected into the subject by solution injection mechanism 124.

While the contrast medium and the saline solution are being injected into the subject respectively by medium injection mechanism 123 and solution injection mechanism 124, the pressures under which the contrast medium and the saline solution are injected are detected in real-time by respective load cells 122 in step S16. Data of a time-dependent graph of the detected pressures is generated in real-time in step S17, and the time-dependent graph is displayed on touch panel 105 in step S18.

During the above injection process in steps S15 through S18, if a malfunction is detected based on the injection pressures in step S19, then an error is displayed as a guidance image on touch panel 105 in step S20, and the injection process is interrupted in step S22.

If the operator makes an input action on touch panel 105 to interrupt the injection process in step S21, then the injection process is also interrupted in step S22. After liquid injector 100 has injected the total amounts of contrast medium and saline solution according to the operating conditions in step S23, liquid injector 100 finishes the injection process, and returns to its initial state in step S24.

While liquid injector 100 is not carrying out the above injection process, the operator may load PC card 106 into card drive 107 and make a certain action to download operating conditions from PC card 106 into RAM 133.

Advantages of the Liquid Injector:

Liquid injector 100 displays on its touch panel 105 schematic images of a plurality of body sections in the shape of a human body. When the operator manually touches and selects one of the schematic images of the body sections, schematic images of a plurality of regions to be imaged which are related to the selected body section are displayed. When the operator manually touches and selects one of the schematic images of the regions to be imaged, data of operation conditions corresponding to the selected region are read, and medium injection mechanism 123 and solution injection mechanism 124 are controlled in operation under the operating conditions.

Consequently, a contrast medium can be injected into the subject under optimum conditions through a highly simple process. As the operator is not required to perform a complex procedure for entering numerical values of an injection rate and a total amount of contrast medium to be injected, the contrast medium is prevented from being injected into the subject under inappropriate conditions due to a mistake that the operator might otherwise make in entering those numerical values.

Since liquid injector 100 displays schematic images of a plurality of body sections in the shape of a human body, the operator is allowed to select any of the body sections easily and reliably. Because schematic images of body sections and regions to be imaged are displayed on touch panel 105 and can directly be manually acted upon, they can be touched and selected easily and reliably.

With liquid injector 100, medium injection mechanism 123 and solution injection mechanism 124 are operated to inject a contrast medium and a saline solution into the subject. Inasmuch as medium injection mechanism 123 and solution injection mechanism 124 are automatically interlinked under operating conditions, the contrast medium and the saline solution can be injected into the subject in interlinked relation to each other without the need for a complex control process.

Liquid injector 100 changes the rate at which the contrast medium is injected with time according to a variable pattern. Therefore, liquid injector 100 allows CT scanner 300 to keep a CT value at a level which approximates an optimum value and hence to capture optimum fluoroscopic images. Since the amount of contrast medium used is held to a minimum required, the contrast medium can be saved, and contributions can be made to the subject's health.

Figure 11:
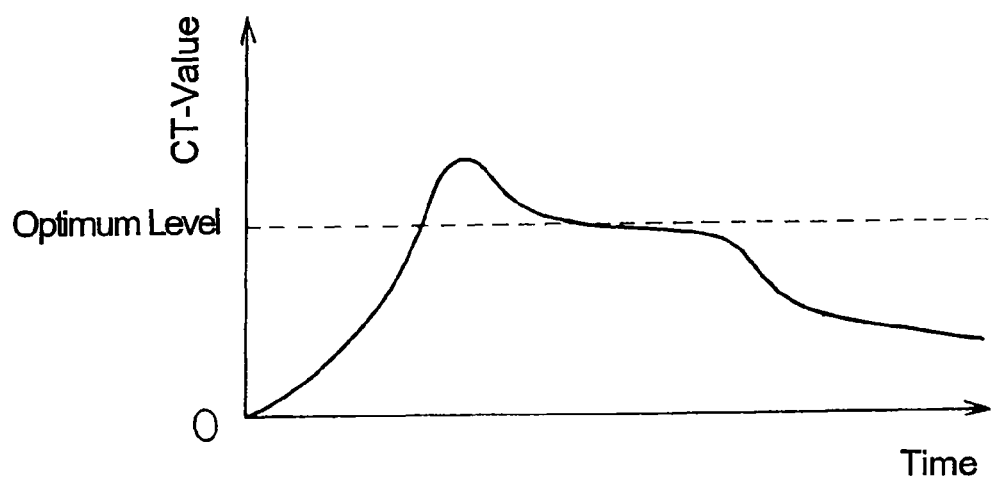
FIG. 11 is a diagram showing a CT value as it varies with time based on the variable pattern of the injection rate shown in FIG. 10.

When an experiment was made in which a contrast medium was injected into the subject according to a variable pattern such that the injection rate was linearly reduced for a certain period of time from the start of injection, and subsequently kept constant, as shown in FIG. 10, it was confirmed that a CT value approximating an optimum value was maintained for a long period of time, as shown in FIG. 11.

The above variable pattern differs from region to region to be imaged, and it would need a tedious and time-consuming process to set and manipulate such different variable patterns. However, liquid injector 100 allows the operator to set an appropriate variable pattern simply by selecting a schematic image of a body section and then a schematic image of a region to be imaged. Therefore, liquid injector 100 can carry out a tedious and time-consuming process based on simple actions on the part of the operator.

While liquid injector 100 is injecting a contrast medium and a saline solution into the subject, liquid injector 100 detects the pressures under which the contrast medium and the saline solution are injected and displays the detected pressures as a graph on touch panel 105. The operator can thus visually confirm changes in the pressures under which the contrast medium and the saline solution are injected in realtime.

When the operator enters the weight of the subject and the type of the contrast medium used into liquid injector 100, liquid injector 100 adjusts the operating conditions depending on the weight of the subject and the type of the contrast medium used. Therefore, the contrast medium can be injected into the subject under better conditions. Furthermore, inasmuch as the total amount of contrast medium to be injected which is adjusted as an operating condition is displayed, the operator can start injecting the contrast medium after having confirmed the total amount of contrast medium to be injected. In addition, the operator can directly adjust the total amount of contrast medium to be injected if desired.

When a schematic image of a region to be imaged is selected, liquid injector 100 automatically sets data of a default body weight and the product name of the previously used contrast medium. If a contrast medium which is the same as the previously used contrast medium is to be injected into a subject who has an average body frame, then the operator is only required to select schematic images of a body section and a region to be imaged, and hence finds the entire setting process quite simple.

Since liquid injector 100 can have operating conditions downloaded from PC card 106, operating conditions of liquid injector 100 can be updated simply and reliably when a new product of contrast medium is sold.

Modifications of the Liquid Injector:

The present invention is not limited to the above embodiment, but various changes or modifications may be made therein without departing from the scope of the invention. For example, although liquid injector 100 according to the above embodiment has medium injection mechanism 123 and solution injection mechanism 124 which serve as liquid injection mechanisms for injecting a contrast medium and a saline solution, the present invention is also applicable to a liquid injector having a single liquid injection mechanism for injecting a contrast medium only.

In the above embodiment, a contrast medium and a saline solution are injected in interlinked relation to each other according to operating conditions. Such operating conditions may be set as various data if desired. For example, in order to confirm the connection of extension tube 210, it has been customary to carry out a test injection session for injecting a contrast medium prior to a main injection session, and such a test injection session may be carried out according to operating conditions.

As disclosed in Japanese patent application No. 2002-363675, it is possible to dilute a contrast medium with a saline solution and inject the diluted contrast medium according to operating conditions. Since an appropriate iodine concentration differs from region to region to be imaged, it has been the conventional practice to replace the contrast medium each time a different region is to be imaged. According to the above embodiment, however, when data of regions to be imaged and types of contrast mediums are entered into liquid injector 100, data of operating conditions are set for appropriately diluting contrast mediums with a saline solution for corresponding regions to be imaged. Therefore, if a contrast medium of high concentration is loaded, together with a saline solution, in liquid injector 100, then it is possible to provide various contrast ratios for various regions to be imaged and capture images of those regions without the need for replacing the loaded contrast medium. The operator thus finds it possible to operate liquid injector 100 with a reduced burden.

Since the iodine concentration can freely be varied by diluting the contrast medium with the saline solution, a contrast medium with an iodine concentration that is not commercially available can be injected into the subject. Though it would be tedious and time-consuming for the operator to dilute the contrast medium manually, liquid injector 100 allows the contrast medium to be diluted appropriately according to operating conditions which can simply be selected.

In the above embodiment, touch panel 105 displays a default numerical value of body weight, and allows the operator to increase or reduce the default numerical value by touching the associated icon for thereby entering a desired body weight. However, it is possible for the operator to enter a numerical value of body weight directly with a ten-key pad (not shown), or for touch panel 105 to display body weight ranges of 10 kg or less, 10-20 kg, etc., for the operator to choose from.

As disclosed in Japanese patent application No. 2002-363675, if a medical record of the subject is available as electronic data, then the body weight of the subject can be read from the medical record of the subject. For example, an information storage medium such as PC card 106 which stores data of an electronic medical record of a subject may be prepared, and the body weight of the subject may be downloaded from the information storage medium into liquid injector 100.

Alternatively, liquid injector 100 may be connected on-line to an external database server (not shown) which stores data of electronic records of subjects, and the body weight of a desired subject may be downloaded from the database server into liquid injector 100.

An electronic body weight meter (not shown) may be connected on-line to liquid injector 100, and the body weight of a subject may be measured in real-time by the electronic body weight meter and the data thereof may be entered into liquid injector 100. Alternatively, since CT scanner 300 has a bed for supporting the subject thereon, the body weight of the subject may be measured using the bed and the data thereof may be entered into liquid injector 100.

In the above embodiment, the data of a body weight is entered into liquid injector 100 as a body item about the body of a human being whose fluoroscopic image is to be captured. However, a body shape, an age, a gender, or the like may be entered as such a body item. As a result of various experiments conducted by the present applicant, it has been confirmed that a body item which greatly affects the capture of a fluoroscopic image of a human being is a body weight only. Therefore, it is meaningful to use only a body weight as a body item to be entered into liquid injector 100.

In the above embodiment, the product names of a plurality of contrast mediums are displayed for the operator to choose from, and the data of an iodine concentration of the selected product name is read. However, it is also possible to display a plurality of iodine concentrations for the operator to choose from, or to allow the operator to enter an iodine concentration directly with a ten-key pad, for example.

In the above embodiment, the data of operating conditions registered for each region to be imaged are adjusted depending on the body weight and iodine concentration that have been entered. However, the data of operating conditions may be registered for a plurality of body weight zones and iodine concentrations, and the data of operating conditions may be selectively read depending on the body weight zone and iodine concentration that have been entered.

Liquid injector 100 according to the present embodiment may be used in combination with a variety of types of CT scanners 300. CT scanners 300 of different types have respective imaging rates as an imaging item which differs from product to product. To cope with such different CT scanners 300, the data of operating conditions may be registered in liquid injector 100 for respective types and imaging rates of CT scanners 300, the data of the types and imaging rates of CT scanners 300 may be displayed for the operator to choose from, and the data of operating conditions corresponding to the selected type and imaging rate may be read.

The data of the types and imaging rates of CT scanners 300 may be displayed for the operator to choose from, and the data of operating conditions corresponding to the selected type and imaging rate may be adjusted. The data of the type and imaging rate of CT scanner 300 may be entered from CT scanner 300 or an information storage medium into liquid injector 100, and the data of corresponding operating conditions may be read or adjusted.

In the above embodiment, operating conditions are downloaded from PC card 106 as an information storage medium into liquid injector 100. Various products may be used as such an information storage medium. Liquid injector 100 may read data from loaded PC card 106 in real-time without copying the data from PC card 106 to RAM 133. Alternatively, the data of operating conditions may be registered in an external database server, and liquid injector 100 may download the data of operating conditions on-line from the external database server.

In the above embodiment, liquid injector 100 updates the data of operating conditions stored in RAM 133 by downloading the data of operating conditions from PC card 106. However, liquid injector 100 may display the data of operating conditions read from RAM 133 on touch panel 105, and the operator may manually correct the displayed data to update the data of operating conditions.

In the above embodiment, touch panel 105 is mounted on the upper surface of main body 103 of liquid injector 100, and injection head 110 is mounted on the upper end of movable arm 106 which is vertically mounted on the side wall of main body 103. However, as shown in FIGS. 14a and 14b, touch panel 105 may directly be connected to injection head 110 parallel thereto.

Figure 14A:
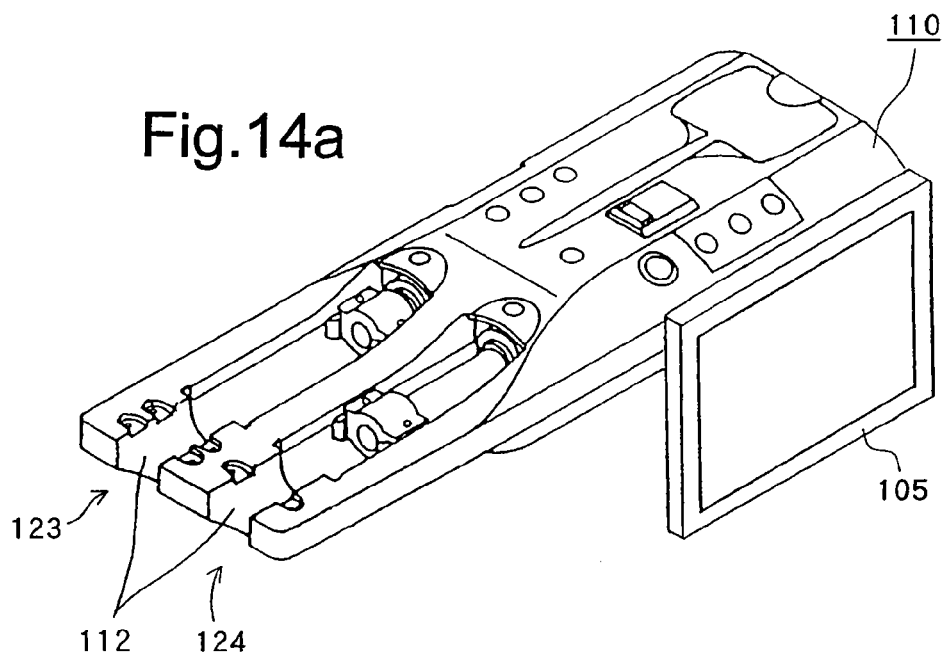
FIGS. 14a and 14b are perspective views showing injection heads according to modifications of the present invention.
Figure 14B:
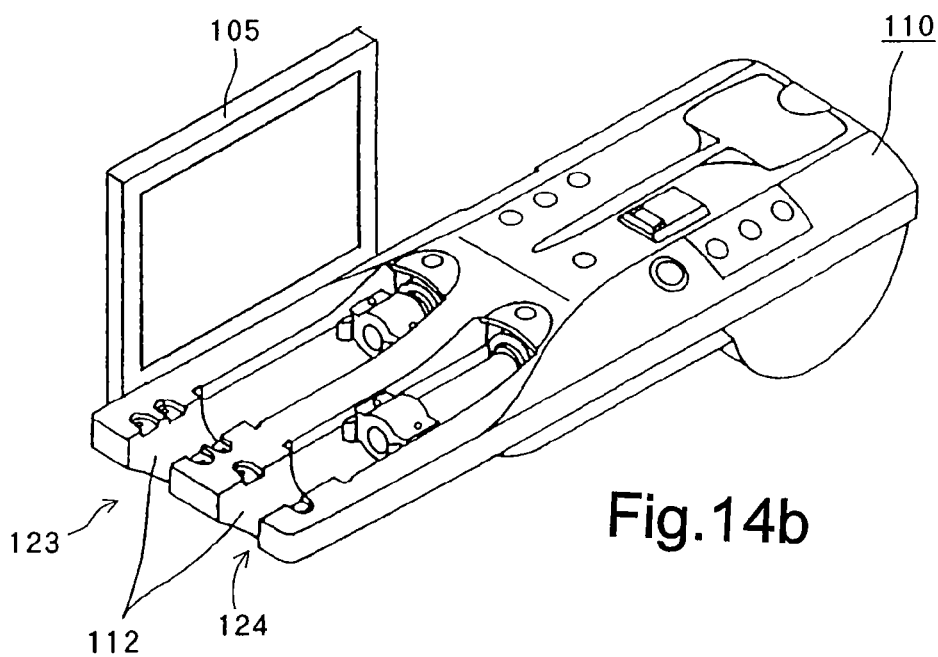

In FIGS. 14a and 14b, since touch panel 105 is positioned adjacent to medium injection mechanism 123 and solution injection mechanism 124, the operator can directly and easily recognize the pressures under which the contrast medium and the saline solution are injected by medium injection mechanism 123 and solution injection mechanism 124 when a graph of the pressures is displayed on touch panel 105.

In the above embodiment, the pressures under which the contrast medium and the saline solution are injected into the subject are calculated from the pressures by which pistons 202 of liquid syringes 200 are pressed. However, the pressures under which the contrast medium and the saline solution are injected into the subject may directly be detected by pressure-sensitive devices which may be placed in liquid syringes 200 or extension tube 210.

In the above embodiment, it has been assumed for the sake of brevity that the pressures under which the contrast medium and the saline solution are injected into the subject are simply calculated from the pressures by which pistons 202 of liquid syringes 200 are pressed. In reality, liquid syringes 200 are presently commercially available in various sizes, and pistons 202 thereof have various end areas.

The pressures under which the contrast medium and the saline solution are injected depend on both the pressures by which pistons 202 are pressed and the end areas of pistons 202. Consequently, if liquid injector 100 employs liquid syringes 200 of various sizes, then the data of end areas of pistons 202 for the various sizes of liquid syringes 200 may be registered, and when the type of liquid syringe 200 used is entered, the data of the end area of corresponding piston 202 may be read.

It is possible to judge the type of the contrast medium contained in liquid syringe 200 set on injection head 110 for thereby dispensing with input actions to enter types of contrast mediums used and hence reducing the burden on the operator. To judge the type of the contrast medium, as disclosed in Japanese patent application No. 2002-021762, injection head 110 may be arranged to acquire identification data of various liquid syringes 200 and the contrast mediums from cylinder adapters (not shown) when liquid syringes 200 are set on injection head 110 by the cylinder adapters.

Alternatively, the data of the types of contrast mediums may be encoded on bar codes (not shown) applied to various liquid syringes 200, and may then be read by injection head 110 for allowing liquid injector 100 to acquire identification data of the contrast mediums.

In the above embodiment, the data of the previously injected contrast medium is saved and used dispensing with unnecessary input actions unless the contrast medium is changed. In addition, the data of the previously imaged region, for example, may also be saved. Specifically, liquid injector 100 may be used in such environments that it captures images of the brain part only for brain surgery applications and images of the heart part only for heart surgery applications. In those environments, the data of the previously imaged region is saved and used dispensing with unnecessary input actions unless the region to be imaged is changed.

In the above embodiment, the injection of liquids with liquid injector 100 and the capture of images with CT scanner 300 are individually manually controlled and carried out. However, liquid injector 100 and CT scanner 300 may communicate with each other for their operations are interlinked.

For example, when the schematic image of a region to be imaged is entered into liquid injector 100, the data of the region to be imaged may be set in CT scanner 300 in response to the entry of the schematic image into liquid injector 100. In this manner, the burden on the operator to operate liquid injector 100 and CT scanner 300 is lessened.

The period of time consumed until the contrast medium reaches a region to be imaged may be set as data in operating conditions, and the region may start being imaged after elapse of a given period of time from the start of injection of the contrast medium under the operating conditions thus set. The period of time consumed until the contrast medium reaches a region to be imaged may be measured in a test injection session by liquid injector 100, and set as data in operating conditions. In this case, the period of time can reliably be set as data in operating conditions.

In the above embodiment, FIG. 10 shows by way of example the variable pattern which is set such that the injection rate is linearly reduced for a certain period of time from the start of injection, and subsequently kept constant. However, the data of various variable patterns may be set based on experimental results, and the injection rate is nonlinearly changed.

Figure 15:
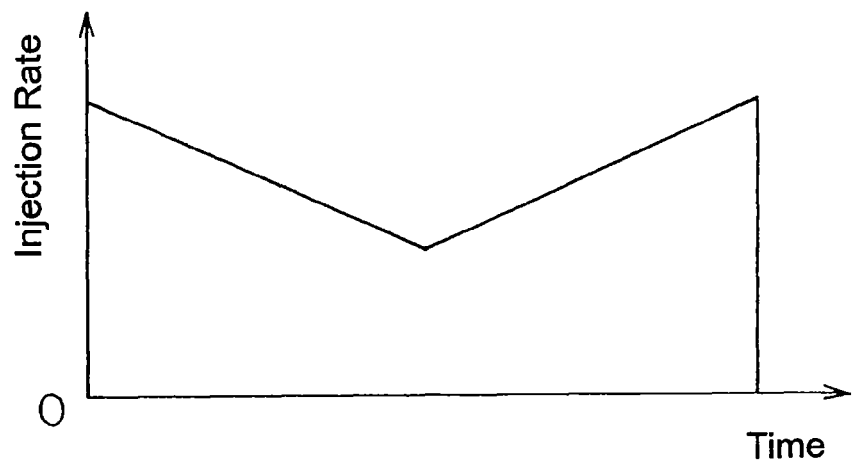
FIG. 15 is a diagram showing a variable pattern of an injection rate according to a modification of the present invention.
Figure 16:
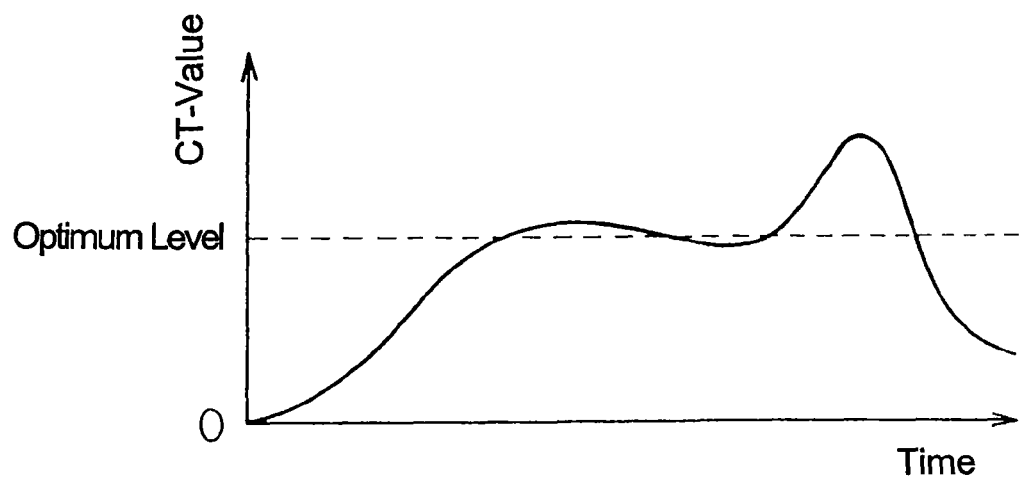
FIG. 16 is a diagram showing a CT value as it varies with time based on the variable pattern of the injection rate shown in FIG. 15.

When the inventor conducted an experiment in which a contrast medium was injected into the subject according to a variable pattern such that the injection rate was linearly reduced for a certain period of time from the start of injection, and subsequently linearly increased, as shown in FIG. 15, it was confirmed that a CT value approximating an optimum value was maintained for a long period of time, as shown in FIG. 16.

Figure 17:
FIG. 17 is a schematic front elevational view showing a displayed image according to a modification of the present invention.

In the above embodiment, schematic images of body sections in the shape of a human body as seen from a lateral side thereof are displayed horizontally in the uppermost portion of the displayed image. However, as shown in FIG. 17, schematic images of body sections in the shape of a human body may be displayed as seen from a front side thereof and may be displayed vertically in a side uppermost portion of the displayed image. The input items should be arranged successively downwardly according to an input sequence as they are effective to make it easy for the operator to understand the input sequence intuitively.

Figure 18:
FIG. 18 is a schematic front elevational view showing a displayed image according to another modification of the present invention.

In the above embodiment, the operator is required to select a region to be imaged and enter a body weight and a contrast medium type. However, as shown in FIG. 18, liquid injector 100 may be arranged to set the data of an injection rate, a total amount of contrast medium to be injected, and a time for which the contrast medium is to be injected, without the need for entering a body weight and a contrast medium type, once the operator selects a region to be imaged.

The above arrangement is particularly effective if a contrast medium type is available in one type only, if a plurality of contrast mediums is available with no essential difference existing therebetween, if a contrast medium to be used is specified and its data are registered in advance, or if only subjects having a standard body weight are to be imaged. In these instances, the burden on the operator is further reduced.

In the above embodiment, CT scanner 300 is used as an imaging diagnostic apparatus, and liquid injector 100 injects a contrast medium for use therewith into subjects. However, an MIR apparatus or a PET apparatus may be used as an imaging diagnostic apparatus, and liquid injector 100 may inject a contrast medium for use therewith into subjects.

In the above embodiment, CPU 131 operates according to the computer program stored in RAM 133 to logically perform the various functions as the various means of liquid injector 100. However, the above functions may be implemented by pieces of hardware, or some of the functions may be stored as software in RAM 133 and the others implemented by pieces of hardware.

While preferred embodiments of the present invention have been described using specific terms, such description is for illustrative purposes only, and it is to be understood that changes and variations may be made without departing from the spirit or scope of the following claims.

The invention claimed is:

1. A liquid injector for injecting at least a contrast medium into a subject whose fluoroscopic image is to be captured by an imaging diagnostic apparatus, wherein said contrast medium is available in a plurality of types having different concentrations of an effective component, said liquid injector, comprising:

a liquid injection mechanism for injecting at least said contrast medium into said subject;

a display/touch panel displaying icons for use in selecting a body portion; and control means for accepting a selection of the icons for selecting the body portion and for controlling operation of said liquid injection mechanism under operating conditions whose data have been read;

said control means is configured:

(i) to read out a base-operation condition including data of:

a predetermined injection time for injection corresponding to the selected body portion, a necessary dose of an effective component of the contrast medium per unit weight of the subject corresponding to the selected body portion, a concentration of the effective component, and an injection rate, (ii) to calculate a necessary volume of the contrast medium based on the read out necessary dose of effective component per unit weight, weight of the subject, and concentration of the effective component, (iii) to make an injection pattern based on the calculated necessary volume of the contrast medium and the base-operation condition, and (iv) to perform the injection of contrast medium based on the injection pattern by controlling the operation of said liquid injection mechanism, wherein the injection rate of the base-operation condition is changed based on the calculated necessary volume of the contrast medium, and wherein the predetermined injection time is unchanged, for all volumes of the contrast medium, when making the injection pattern, whereby a timing of an optimum concentration of the contrast medium will be substantially unchanged for all volumes of the contrast medium.

2. The liquid injector according to claim 1, wherein the display/touch panel is adapted to display a plurality of body sections, as the body portion, in schematic images of a shape of a human body, and wherein, the control means is adapted to accept a selection of one of said body sections when one of the displayed body sections is selected; to display at least one of a plurality of regions to be imaged of the human body, as the body portion, in schematic images of shapes of the regions; and to accept a selection of one of said regions to be imaged when one of said displayed regions to be imaged is selected.

3. The liquid injector according to claim 2, wherein the display/touch panel displays the body sections in a shape of a horizontally displayed human body image.

4. The liquid injector according to claim 2, wherein the display/touch panel displays the body sections in a shape of a vertically displayed human body image.

5. The liquid injector according to claim 1, wherein the control means is further adapted to display items relating to the subject's body; to accept an input of selecting one of the body items; and to adjust the operating conditions based on the selected body item.

6. The liquid injector according to claim 5, wherein the body item includes at least one of a body weight, body shape, age and gender.

7. The liquid injector according to claim 1, wherein the control means is configured to read data of a subject's body weight from an external database server.

8. The liquid injector according to claim 1, wherein the control means is configured to read data of a subject's body weight from an information storage medium.

9. The liquid injector according to claim 1, wherein the control means is configured to read data of a subject's body weight from an electronic scale to measure weight.

10. The liquid injector according to claim 1, wherein the display/touch panel displays a predetermined body weight as a default value.

11. The liquid injector according to claim 1, wherein the control means is configured to detect in real-time a pressure of at least the contrast medium during injection and to display in real-time the detected pressure on the display/touch panel.

12. The liquid injector according to claim 1, wherein the liquid injection mechanism comprises a contrast medium injection mechanism for injecting a contrast medium and a solution injection mechanism for injecting a saline solution, said base-operation condition comprises a pattern wherein the injection of the contrast medium and the injection of the saline solution are interlinked for the selected area to be imaged, and said control means further reads out the base-operation, and performs the interlinked injection of said contrast medium and said saline solution by controlling said contrast medium mechanism and said solution injection mechanism.

13. The liquid injector according to claim 1, further comprising an injection head and a console.

14. The liquid injector according to claim 13, wherein the injection head is provided with the display/touch panel.

15. The liquid injector according to claim 13, wherein the console is provided with the display/touch panel.

16. The liquid injector according to claim 13, wherein the injection head is configured to hold at least one pre-filled syringe.

* * * * *